(12) United States Patent
Aust et al.

(10) Patent No.: US 7,175,834 B2
(45) Date of Patent: Feb. 13, 2007

(54) SUNSCREEN COMPOSITION WITH ENHANCED SPF AND WATER RESISTANT PROPERTIES

(75) Inventors: Duncan T. Aust, Carson City, NV (US); James M. Wilmott, Shoreham, NY (US); James A. Hayward, Stony Brook, NY (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 11/114,668

(22) Filed: Apr. 26, 2005

(65) Prior Publication Data

US 2005/0186160 A1    Aug. 25, 2005

Related U.S. Application Data

(63) Continuation of application No. 10/332,393, filed on Apr. 29, 2003, now abandoned, and a continuation of application No. PCT/US01/21588, filed on Jul. 9, 2001.

(60) Provisional application No. 60/216,573, filed on Jul. 7, 2000.

(51) Int. Cl.
- A61Q 17/04 (2006.01)
- A61Q 17/00 (2006.01)
- A61Q 19/00 (2006.01)
- A61K 8/00 (2006.01)
- A61K 8/04 (2006.01)

(52) U.S. Cl. ............ 424/59; 424/60; 424/400; 424/401

(58) Field of Classification Search ............ 424/59, 424/60, 400, 401
See application file for complete search history.

(56) References Cited

U.S. PATENT DOCUMENTS

| | | | |
|---|---|---|---|
| 3,208,911 A | 9/1965 | Opplinger | 167/87 |
| 3,964,500 A | 6/1976 | Drakoff | 132/7 |
| 4,152,416 A | 5/1979 | Spitzer et al. | 424/46 |
| 4,172,122 A | 10/1979 | Kubik et al. | 424/59 |
| 4,193,989 A | 3/1980 | Teng et al. | 424/60 |
| 4,341,799 A | 7/1982 | Good | 424/365 |
| 4,364,837 A | 12/1982 | Pader | 252/173 |
| 4,457,911 A | 7/1984 | Conner et al. | 424/59 |
| 4,465,619 A | 8/1984 | Boskamp | 252/540 |
| 4,515,774 A | 5/1985 | Conner et al. | 424/59 |
| 4,533,254 A | 8/1985 | Cook et al. | 366/176 |
| 4,613,499 A | 9/1986 | Conner | 424/59 |
| 4,680,144 A | 7/1987 | Conner | 560/49 |
| 4,788,006 A | 11/1988 | Bolich, Jr. et al. | 252/550 |
| 5,061,481 A | 10/1991 | Suzuki et al. | 424/63 |
| 5,093,107 A | 3/1992 | Matravers | 424/59 |
| 5,145,669 A | 9/1992 | Kwak et al. | 424/59 |
| 5,152,983 A | 10/1992 | Nambudiry et al. | 424/60 |
| 5,160,738 A | 11/1992 | Macaulay et al. | 424/401 |
| 5,188,331 A | 2/1993 | Baines | 248/538 |
| 5,204,090 A | 4/1993 | Han | 424/59 |
| 5,207,998 A | 5/1993 | Robinson et al. | 424/59 |
| 5,306,485 A | 4/1994 | Robinson et al. | 424/59 |
| 5,417,961 A | 5/1995 | Nearn et al. | 424/59 |
| 5,441,726 A | 8/1995 | Mitchnick et al. | 424/59 |
| 5,460,804 A | 10/1995 | Krzysik | 424/60 |
| 5,486,352 A | 1/1996 | Guerrero | 424/59 |
| 5,486,353 A | 1/1996 | Billia et al. | 424/59 |
| 5,633,403 A | 5/1997 | Gallagher et al. | 564/517 |
| 5,637,291 A * | 6/1997 | Bara et al. | 424/59 |
| 5,637,718 A | 6/1997 | Bird et al. | 546/315 |
| 5,679,656 A | 10/1997 | Hansenne | 514/54 |
| 5,700,451 A | 12/1997 | Yue et al. | 424/59 |
| 5,705,145 A | 1/1998 | Miklean et al. | 424/59 |
| 5,741,480 A | 4/1998 | Ascione | 424/59 |
| 5,858,334 A | 1/1999 | Ascione et al. | 424/59 |
| 5,916,541 A | 6/1999 | Stewart | 424/59 |
| 5,958,297 A | 9/1999 | Primdahl | 252/373 |
| 5,961,961 A | 10/1999 | Dobkowski et al. | 424/59 |
| 5,968,528 A | 10/1999 | Deckner et al. | 424/401 |
| 5,972,359 A | 10/1999 | Sine et al. | 424/401 |
| 5,976,510 A | 11/1999 | Cernasov et al. | 424/59 |
| 5,980,871 A | 11/1999 | Lukenbach et al. | 424/59 |
| 5,997,890 A | 12/1999 | Sine et al. | 424/401 |
| 6,831,107 B2 * | 12/2004 | Dederen et al. | 514/777 |

* cited by examiner

Primary Examiner—Shelley A. Dodson
(74) Attorney, Agent, or Firm—Michelle J. Burke

(57) ABSTRACT

The present invention relates to a sunscreen formulation which exhibits superior ultraviolet protection and water resistance than prior art sunscreen compositions. The sunscreen formulation comprises (a) a dispersion comprising a sunscreen active agent and (b) a base composition comprising a rheological modifying agent and water. The sunscreen formulation is substantially free of surfactants. According to a preferred embodiment, the sunscreen active agent is ethylhexylmethoxycinnamate, butylmethoxydibenzoylmethane, or a combination thereof. The sunscreen formulation preferably comprises a phosphorylated starch derivative as a rheological modifying agent. Another embodiment of the present invention is a method of protecting skin or hair from ultraviolet radiation by applying an effective amount of the sunscreen formulation of the present invention to the skin or hair.

35 Claims, No Drawings

SUNSCREEN COMPOSITION WITH ENHANCED SPF AND WATER RESISTANT PROPERTIES

This application is continuation of U.S. application Ser. No. 10/332,393, filed Apr. 29, 2003, now abandoned, claiming priority from U.S. Provisional Application Ser. No. 60/216,573, filed Jul. 7, 2000 and a Continuation of PCT/US01/21588, filed Jul. 9, 2001, all of which are herein incorporated by reference.

FIELD OF THE INVENTION

The present invention relates to a surfactant-free sunscreen composition comprising a base and dispersion of a sunscreen active agent, and a method of use thereof.

BACKGROUND OF THE INVENTION

Mild sweating or swimming is often sufficient to remove most commercially available sunscreen formulations from a person's skin. The ease with which these sunscreens are washed off by water necessitates multiple applications to the skin. The need to repeatedly apply sunscreen is costly to the consumer, inconvenient and tends to cause consumers to delay reapplication of the sunscreen which may lead to sunburn. Since most sunscreen active agents are hydrophobic, one method attempted to overcome the problem of easy removal with water and to improve water resistivity of sunscreen formulations is to prepare water-in-oil or oil-in-water emulsions, however, products formed from these emulsions are aesthetically unpleasing and feel greasy or oily and heavy. In addition, surfactants, added to emulsions to reduce the surface tension between the hydrophobic and hydrophilic ingredients, unfortunately reduce the water resistivity of these formulations because surfactants (and other emulsifiers) facilitate the removal of sunscreen from the surface of the skin when it comes in contact with water. Thus, these emulsion-based formulations often include waterproofing agents, such as high molecular weight resins such as high molecular weight silicon fluids, to improve the water resistant properties of the sunscreen formulations. However, addition of waterproofing agents adds cost to the formulations and causes a deterioration of the product's aesthetic properties.

Accordingly, it is desirable to produce a stable surfactant-free formulation comprising an oil-in-water dispersion which is highly water resistant, maintains high levels of sunscreen protection, provides provide uniform skin coverage and is aesthetically pleasing, i.e., does not feel oily or greasy.

SUMMARY OF THE INVENTION

The present invention provides a sunscreen formulation comprising (a) a dispersion comprising a sunscreen active agent and (b) a base composition comprising a rheological modifying agent and water. The sunscreen formulation is substantially free of surfactants.

The dispersion has a particle size of from about 50 to 1000 nm, preferably from about 300 to 800 nm.

The dispersion contains suspended particles in an amount of from about 0.01 to about 70% by weight of suspended particles, based upon 100% weight of total dispersion. Preferably, the dispersion contains from about 1.0 to 60% by weight of suspended particles, based upon 100% weight of total dispersion.

The base composition typically comprises from about 0.001 to about 50% and preferably from about 0.01 to about 10%, and more preferably from about 0.1 to about 5% by weight of rheological modifying agents. The base composition typically comprises from about 0.001 to about 99.99%, preferably from about 1 to about 99.99%, and more preferably from about 20 to about 99.99% by weight of water.

Generally, the sunscreen formulation contains from about 0.1 to about 60% by weight, preferably from about 1 to about 60% by weight, and more preferably from about 10 to about 50% by weight of the sunscreen agent containing dispersion, based upon 100% weight of total sunscreen formulation. The sunscreen formulation also typically contains from about 0.01 to about 100% by weight, preferably from about 0.1 to about 90% by weight, and more preferably from about 5 to about 80% by weight of the base composition, based upon 100% weight of total sunscreen formulation.

The dispersion is preferably prepared by high pressure/high shear processing.

According to a preferred embodiment, the sunscreen active agent is selected from the group consisting of ethylhexylmethoxycinnamate, butylmethoxydibenzoylmethane, octocrylane, octyl salicylate, benzophenone-3, or a combination thereof.

The base composition preferably comprises a phosphorylated starch derivative as a rheological modifying agent.

The sunscreen formulation of the present invention exhibits superior ultraviolet protection to the skin and hair and demonstrates enhanced water resistance over prior art sunscreen compositions containing emulsions.

Another embodiment of the present invention is a method of protecting skin or hair from ultraviolet (UV) radiation by applying an effective amount of the sunscreen formulation of the present invention to the skin or hair. In addition to providing enhanced protection from harmful rays, the formulation remains on the skin or hair for longer periods of time due to enhanced water resistance.

A most preferred sunscreen formulation of the invention comprises a dispersion comprising water, ethylhexylmethoxycinnamate, butylmethoxydibenzoylmethane, cyclomethicone, and phospholipids.

DETAILED DESCRIPTION OF THE INVENTION

The inventors of the present invention have found that high pressure high shear (HPHS) dispersions, which are produced devoid of traditional surfactants, overcome the aforementioned problems found in current emulsion-based formulations. The compositions of the present invention exhibit a high degree of uniformity as a consequence of the high pressure and high shear process by which the aqueous and hydrophobic phases are mixed. The particles in the suspended phase of the dispersion typically have a very small particle size of less than 1000 nm.

The sunscreen formulation of the present invention exhibits superior ultraviolet protection (against UV-A (320–400 nm) and UV-B (280–320 nm) radiation) and water resistance than prior art sunscreen compositions. For purposes of the present invention, water resistance is defined as the inability of the material to be removed from the surface to which it is applied in the presence of water. Since the sunscreen formulation is highly water resistant, frequent application of the formulation is not needed, thereby reducing the likelihood of sunburn and the cost to the consumer. Furthermore, since dispersions of the sunscreen agent are homogeneous, the sunscreen agent in the formulation applies uniformly and evenly to the skin and hair to provide comprehensive coverage.

Dispersions of Sunscreen Agents

The term "dispersion" as used herein refers to a suspension of liquid or solid particles of colloidal size or larger in a liquid medium. Generally, the dispersion contains suspended particles, such as oil particles (or oil droplets), having a diameter less than about 1000 nm. The sunscreen agent is typically incorporated into the dispersion as suspended particles. The diameter of the suspended particles preferably ranges from about 50 nm to about 1000 nm and more preferably from about 300 to about 800 nm. Preferably, the suspended particles contain one or more lipophilic materials. The suspended particles may have a charge as determined by zeta potential measurements. The dispersion is preferably prepared by high pressure/high shear mixing, such as described in U.S. Pat. No. 4,533,254.

High pressure or high shear mixing maybe be performed in equipment which includes homogenizers such as a Microfluidizer, DeBee high pressure homogenizer, a french press and a Gaulin homogenizer or "Rotor Stator" devices such as a Symex mill, a Silverson mill and a Ross mill.

The dispersion containing the suspended particles generally contains from about 0.01 to about 70% by weight of suspended particles, based upon 100% weight of total dispersion. Preferably, the dispersion contains from about 1.0 to about 60% by weight of suspended particles, based upon 100% weight of total dispersion.

The dispersion may contain hydrophobic active agents and hydrophobic adjuvants. A hydrophobic active agent or hydrophobic adjuvant is an active agent or adjuvant that has a non polar property which makes it essentially insoluble in water or water and polar solvent solutions. Hydrophobic active agents and hydrophobic adjuvants of the present invention include, but are not limited to, partially and fully hydrophobic active agents and partially and fully hydrophobic adjuvants. For example, hydrophobic active agents encompassed by the present invention include compounds and complexes which contain a hydrophobic moiety.

Suitable sunscreen agents include, but are not limited to, agents that absorb ultraviolet radiation, such as UV-A (320–400 nm) and UV-B (280–320 nm) radiation. Preferred sunscreen agents include those which form a physical and/or chemical barrier between UV radiation and the surface to which they are applied. Non-limiting examples of suitable sunscreen agents include ethylhexylmethoxycinnamate (OMC), butylmethoxydibenzoylmethane, methoxydibenzoylmethane, avobenzone, benzophenone-3, octacrylene, titanium dioxide, zinc oxide, aminobenzoic acid, cinoxate, dioxybenzone, homosalate, menthyl anthranilate, octocrylene, octisalate, oxybenzone, padimate O, phenylbenzimidazole sulfonic acid, sulisobenzone, trolamine salicylate and any combination of any of the foregoing. According to a preferred embodiment, the dispersion contains ethylhexyl methoxycinnamate, butylmethoxydibenzoylmethane, or a combination thereof.

Base Composition

Rheological modifying agents within the scope of the invention include any substance which increases or decreases the viscosity of the sunscreen formulation. Suitable rheological modifying agents include, but are not limited to, phosphorylated starch derivatives, carbohydrate based rheological modifying agents, polymeric and copolymeric rheological modifying agents, inorganic rheological modifying agents, protein rheological modifying agents, polypeptide rheological modifying agents, and any combination of any of the foregoing.

The term "phosphorylated starch derivative" includes, but is not limited to, starches containing a phosphate group. Suitable phosphorylated starch derivatives include, but are not limited to, hydroxyalkyl starch phosphates, hydroxyalkyl distarch phosphates, and any combination of any of the foregoing. Non-limiting examples of hydroxyalkyl starch phosphates and hydroxyalkyl distarch phosphates include hydroxyethyl starch phosphate, hydroxypropyl starch phosphate, hydroxypropyl distarch phosphate (including sodium hydroxypropyl starch phosphate), and any combination of any of the foregoing.

Non-limiting examples of suitable carbohydrate based rheological modifying agents include algin and derivatives and salts thereof, such as algin, calcium alginate, propylene glycol alginate, and ammonium alginate; carrageenan (*Chondrus crispus*) and derivatives and salts thereof, such as calcium carrageenan and sodium carrageenan; agar; cellulose and derivatives thereof, such as carboxymethyl hydroxyethylcellulose, cellulose gum, cetyl hydroxyethylcellulose, hydroxyethylcellulose, hydroxypropylcellulose, hydroxypropyl methylcellulose, methylcellulose, ethylcellulose, and cellulose gum; chitosan and derivatives and salts thereof, such as hydroxypropyl chitosan, carboxymethyl chitosan, and chitin; gellan gum; guar (*Cyanopsis tetragonoloba*) and derivatives thereof, such as guar hydroxypropyltrimonium chloride and hydroxypropyl guar; hyaluronic acid and derivatives thereof, such as sodium hyaluronate; dextran and derivatives thereof; dextrin; locust bean (*Ceratonia siliqua*) gum; starches, such as starch polyacrylonitrile copolymer-potassium salt and starch polyacrylonitrile copolymer-sodium salt; pectin; sclerotium gum; tragacanth (*Astragalus gummifer*) gum; xantham gum and derivatives thereof; and any combination of any of the foregoing.

Non-limiting examples of suitable polymeric and copolymeric rheological modifying agents include acrylates, methacrylates, polyethylene and derivatives thereof, and any combination of any of the foregoing. Suitable acrylates and methacrylates include, but are not limited to, carbomer and derivatives and salts thereof, acrylate/$C_{10}$–$C_{30}$ alkyl acrylate crosspolymer, acrylate/ceteth-20 itaconate copolymer, acrylate/ceteth-20 methacrylate copolymers, acrylate/steareth-20 methacrylate copolymers, acrylate/steareth-20 itaconate copolymers, acrylate/steareth-50 acrylate copolymers, acrylate/VA crosspolymers, acrylate/vinyl isodecanoate crosspolymers, acrylic acid/acrylonitrogen copolymers, ammonium acrylate/acrylonitrogen copolymers, glyceryl polymethacrylate, polyacrylic acid, PVM/MA decadiene crosspolymer, sodium acrylate/vinyl isodecanoate crosspolymers, sodium carbomer, ethylene/acrylic acid copolymer, ethylene/VA copolymer, acrylate/acrylamide copolymer, acrylate copolymers, acrylate/hydroxyester acrylate copolymers, acrylate/octylarylamide copolymers, acrylate/PVP copolymers, AMP/acrylate copolymers, butylester of PVM-MA copolymer, carboxylate vinylacetate terpolymers, diglycol/CHDM/isophthalates/SIP copolymer, ethyl ester of PVM-MA copolymer, isopropyl ester of PVM-MA copolymer, octylacrylamide/acrylate/butylaminoethyl methacrylate copolymers, polymethacrylamidopropyltrimonium chloride, propylene glycol oligosuccinate, polyvinylcaprolactam, PVP, PVP/dimethylaminoethylmethacrylate copolymer, PVP/DMAPA acrylate copolymers, PVP/carbamyl polyglycol ester, PVP/VA copolymer, PVP/VA vinyl propionate copolymer, PVP/vinylcaprolactam/DMAPA acrylate copolymers, sodium polyacrylate, VA/butyl maleate/ isobornyl acrylate copolymers, VZ/crotonates copolymer, VA/crotonates vinyl neodecanoate copolymer, VA crotonates/vinyl propionate copolymer, vinyl caprolactam/PVP/ dimethylaminoethylmethacrylate copolymer, and any combination of any of the foregoing.

Non-limiting examples of suitable inorganic thickening agents include clays and derivatives thereof, silicates, silicas and derivatives thereof, and any combination of any of the foregoing. Suitable clays and derivatives thereof include, but are not limited to, bentonite and derivatives thereof, such as quaternium-18 bentonite; hectorite and derivatives thereof, such as quaternium-18 dectorite; montmorillonite; and any combination of any of the foregoing. Suitable silicates include, but are not limited to, magnesium aluminum silicate, sodium magnesium silicate, lithium magnesium silicate, tromethamine magnesium aluminum silicate, and any combination of any of the foregoing. Suitable silicas and derivatives thereof include, but are not limited to, hydrated silica, hydrophobic silica, and any combination of any of the foregoing.

Suitable protein and polypeptide rheological modifying agents include, but are not limited to, proteins and derivatives and salts thereof, polypeptides and derivatives and salts thereof, and any combination of any of the foregoing. Non-limiting examples of protein and polypeptide rheological modifying agents include albumin, gelatin, keratin and derivatives thereof, fish protein and derivatives thereof, milk protein and derivatives thereof, wheat protein and derivatives thereof, soy protein and derivatives thereof, elastin and derivatives thereof, silk protein and derivatives thereof, and any combination of any of the foregoing.

Preferred rheological modifying agents include, but are not limited to, carbomer, acrylate/alkyl acrylate crosspolymers, acrylate/vinyl isododecanoate crosspolymer, xantham gum, locust bean gum, guar gum, and any combination of any of the foregoing. A more preferred combination of rheological modifying agents comprises carbomer and an acrylate/alkyl acrylate copolymer, such as an acrylate/ $C_{10}$–$C_{30}$ alkyl acrylate crosspolymer. According to the International Cosmetic Ingredient Dictionary and Handbook ($7^{th}$ Ed., The Cosmetic, Toiletry, and Fragrance Association), carbomer is a homopolymer of acrylic acid crosslinked with an allyl ether of pentaerythritol, an allyl ether of sucrose, or an allyl ether of propylene. The term "acrylate/alkyl acrylate crosspolymer" includes, but is not limited to, copolymers of alkyl acrylates with one or more monomers of acrylic acid, methacrylic acid, or one of their short chain (i.e. $C_{-1-4}$ alcohol) esters, wherein the crosslinking agent is, for example, an allyl ether of sucrose or pentaerytritol. Preferably, the alkyl acrylates are $C_{10}$–$C_{30}$ alkyl acrylates. Examples of such copolymers include, but are not limited to, those commercially available as Carbopol™ 1342, Carbopol™ 1382, Pemulen™ TR-1, and Pemulen™ TR-2, from Goodrich Specialty Chemicals of Cleveland, Ohio.

Preferred rheological modifying agents include, but are not limited to hydrophilic gelling agents, such as carboxyvinyl polymers (carbomer), acrylic copolymers (e.g. acrylate/alkyl acrylate copolymers), polyacrylamides, polysaccharides (e.g. hydroxypropylcellulose), natural gums, clays, and any combination of any of the foregoing.

The base composition typically comprises from about 0.001 to about 50% and preferably from about 0.01 to about 10%, and more preferably from about 0.1 to about 5% by weight of rheological modifying agents. The base composition typically comprises from about 0.001 to about 99.99%, preferably from about 1 to about 99.99%, and more preferably from about 20 to about 99.99% by weight of water.

Sunscreen Formulation

Generally, the sunscreen formulation contains from about 0.1 to about 60% by weight, preferably from about 1 to about 60% by weight, and more preferably from about 10 to about 50% by weight of the sunscreen agent containing dispersion, based upon 100% weight of total sunscreen formulation. The sunscreen formulation also typically contains from about 0.01 to about 100% by weight, preferably from about 0.1 to about 90% by weight, and more preferably from about 5 to about 80% by weight of the base composition, based upon 100% weight of total sunscreen formulation.

The sunscreen formulation is substantially free of (emulsifying) surfactants. The composition preferably contains less than about 3% by weight and more preferably less than about 1% by weight of surfactants, based upon 100% weight of total composition. Generally, hydrophobic ingredients which are not in the form of dispersions are not included in the sunscreen formulation, or at least not in any substantial amounts.

The composition of the present invention may also include active agents and adjuvants, including those described in *Remington's Pharmaceutical Sciences,* $19^{th}$ Edition, A. R. Gennaro (1995). Hydrophobic active agents and hydrophobic adjuvants are preferably incorporated into the formulation as dispersions.

The sunscreen formulation may be a cream, gel, lotion, serum or spray.

The sunscreen formulation of the present invention may be topically applied to the skin or hair of an animal, such as a human, to protect skin or hair from ultraviolet radiation and reduce water penetration in the skin and hair.

Active Agents

The sunscreen dispersions of the current invention can be added alone to the compatible base compositions or combined with other physiologically active materials or aesthetic modifying agents.

Suitable active agents include, but are not limited to, anti-acne agents, antimicrobial agents, antiinflammatory agents, analgesics, antierythemal agents, antipruritic agents, antiedemal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, amino acids, peptides, minerals, ceramides, biohyaluronic acids, and any combination of any of the foregoing.

Aesthetic Modifying Agents

The composition preferably includes at least one aesthetic modifying agent. An aesthetic modifying agent is a material that imparts desirable tactile, olfactory, taste or visual properties to the surface to which the composition is applied. The aesthetic modifying agent may be hydrophobic or hydrophilic. The aesthetic modifying agent is preferably hydrophobic and is more preferably an oil, wax, solid or paste.

A dispersion of one or more hydrophobic aesthetic modifying agents is preferably prepared before the hydrophobic aesthetic modifying agents are incorporated into the composition. The hydrophobic aesthetic modifying agents may be dispersed into an aqueous phase by methods known in the art, such as by ultra high shear mixing and microfluidization.

The final composition may be prepared by mixing the dispersions containing the hydrophobic aesthetic modifying agents with the base composition and any other adjuvants. Since the hydrophobic aesthetic modifying agents are added to the base composition as dispersions, heating and other expensive processing steps are not required to obtain a homogenous final composition.

An example of an aesthetic modifying agent is a mono, di, tri or poly alkyl ester or ether of a di, tri, or polyhydroxy compound, such as ethylene glycol, propylene glycol, glycerin, sorbitol or other polyol compound.

An example of a hydrophobic aesthetic modifying agent is a compound having the formula $C_nH_{(2n+2-m)}$ wherein n is an integer greater than or equal to 6 and m is 0 or an even integer no greater than n. Such compounds include, but are not limited to, saturated and unsaturated, linear, branched, and cyclic hydrocarbon chains. Preferred examples of such compounds include, but are not limited to mineral oil, petrolatum, permethyl fluids, polybutylenes, and polyisobutylenes.

Another example of a hydrophobic aesthetic modifying agent has the formula

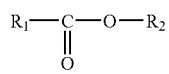

or the formula

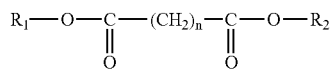

wherein $R_1$ is a saturated or unsaturated, linear, branched or cyclic $C_1$–$C_{24}$ alkyl group; $R_2$ is hydrogen or a saturated or unsaturated, liner, branched or cyclic $C_1$–$C_{24}$ alkyl group; and n is an integer from 0 to 20. Examples of such aesthetic modifying agents include, but are not limited to, isopropyl palmitate and diisopropyl adipate. Examples of such esters and ethers include but are not limited to, saturated and unsaturated, linear and branched vegetable oils, such as soybean oil, babassu oil, castor oil, cottonseed oil, chinese tallow oil, crambe oil, perilla oil, danish rapeseed oil, rice bran oil, palm oil, palm kernel oil, olive oil, linseed oil, coconut oil, sunflower oil, safflower oil, peanut oil and corn oil. Preferred saturated and unsaturated vegetable oils are those having fatty acid components with 6 to 24 carbon atoms. A more preferred vegetable oil is soybean oil.

Yet another aesthetic modifying agents are based on silicone chemistry. Silicone may provide lubrication and/or shine to the composition. Preferably, the silicone is insoluble in water. Suitable water-insoluble silicone materials include, but are not limited to, polyalkylsiloxanes, polyarylsiloxanes, polyalkylarylsiloxanes, polysiloxane gums and polyethersiloxane copolymers. Examples of suitable silicone materials are disclosed in U.S. Pat. Nos. 4,788,006; 4,341,799; 4,152,416; 3,964,500; 3,208,911; 4,364,837 and 4,465,619, all of which are incorporated herein by reference.

Another suitable hydrophobic material which can be suspended in the composition has the formula

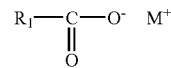

wherein $R_1$ is a saturated or unsaturated, linear, branched or cyclic alkyl having 2 to 24 carbon atoms; $M^{(+)}$ is $N^+R_2R_3R_4R_5$; where $R_2$, $R_3$ and $R_4$ are hydrogen or a saturated or unsaturated, linear or branched alkyl or hydroxyalkyl having from 1 to 10 carbon atoms; and $R_5$ is a saturated or unsaturated, linear, branched or cyclic alkyl or substituted alkyl having 2 to 24 carbon atoms. An example of such a material is lauramine oleate.

Other Adjuvants

Suitable adjuvants which may be incorporated in the sunscreen formulation include, but are not limited to, pH adjusters, emollients, conditioning agents, moisturizers, chelating agents, gelling agents, colorants, fragrances, odor masking agents, UV stabilizer, preservatives, and any combination of any of the foregoing. Preferred pH adjusters include, but are not limited to, aminomethyl propanol, aminomethylpropane diol, triethanolamine, triethylamine, citric acid, sodium hydroxide, acetic acid, potassium hydroxide, lactic acid, and any combination of any of the foregoing.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cetrimonium chloride; diphenyl dimethicone; propylene glycol; glycerin; quaternary amines; and any combination of any of the foregoing.

Suitable preservatives include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylchloroisothiazolinone, methylisothiazolinone, and any combination of any of the foregoing. The sunscreen formulation generally contains from about 0.001% to about 20% and preferably from about 0.1 to about 10% by weight of preservatives, based upon 100% weight of total sunscreen formulation.

EXAMPLES

The following examples are intended to describe the present invention without limitation.

Example 1

A. Preparation of Dispersions

Compositions 1–5 in Table 1 are dispersions of organic sunscreens in water. These dispersions were manufactured as follows:
1. The ingredients in phase "A" were combined and mixed, and the mixture was heated until a uniform solution was formed.
2. The ingredients in phase "B" were combined and mixed at ambient conditions until a uniform solution was formed.
3. Phase A was combined with phase B using high shear homogenization followed by high pressure/high shear mixing until a particle size of less than 1000 nm and preferably 250–500 nm was obtained.

TABLE 1

| | SPF Lotion (% w/w) | COMPOSITION | | | | |
|---|---|---|---|---|---|---|
| Phase | Ingredient | 1 | 2 | 3 | 4 | 5 |
| A | Escalol 557[1] | 30.0 | 37.5 | 25.0 | 21.4 | 30.0 |
| | Parsol 1789[2] | 12.0 | 10.0 | 6.0 | — | — |
| | Uvinul N-539-SG[3] | — | — | — | 28.6 | — |
| | Escalol 567[1] | — | — | 8.0 | — | 10.0 |
| | Crodanol ISNP[7] | — | — | 10.5 | — | — |
| | Silox Lemon Balm[8] | 5.0 | 1.8 | — | — | — |
| B | Water Deionized | q.s. | q.s | q.s. | q.s | q.s. |
| | Basis LP-20H[4] | 1.5 | 1.50 | 2.0 | 2.0 | 1.5 |
| | Phospholipin 80H[5] | — | 0.25 | 0.2 | 0.2 | 0.2 |
| | Butylene Glycol[6] | — | — | 4.0 | 2.5 | — |
| | Germazide MPB[8] | 1.5 | 1.85 | 2.0 | 2.2 | 2.0 |
| | Potassium Sorbate[9] | 0.40 | 0.40 | — | — | — |

[1]Ethylhexyl cinnamate; ISP Corporation.
[2]Butylmethoxydibenzoylmethane; Roche Chemical.
[3]Octacrylene; BASF.
[4]Benzophenone-3; Ikeda
[5]American Lecithin;
[6]Phoenix Chemical;
[7]Croda;
[8]The Collaborative Group, Ltd.;
[9]TRIK B. Preparation of Conventional Emulsion Composition 6 in Table 2 is an example of a finished goods formulation comprising an emulsion, prepared using conventional materials and processing. This emulsion was manufactured as follows:
1. Phase A was mixed until homogenous.
2. The contents of Phase B was added to A (step 1). The mixture was heated on a water bath to 75–80° C., and propel mixed until homogenous.
3. Phase C was heated to 80° C. on a water bath until homogenous, and Phase D was added; the temperature was maintained at 80° C.
4. Phase (C+D) (step 3) was added to Phase (A+B) (step 2) at approximately 80° C.
5. The mixture of step 4 was homogenized using a Silverson mill for about 5 minutes.
6. The homogenate was cooled using a cold water bath. When the temperature was approximately 40° C., Phase E was added, and the mixture was mixed using a propel.
7. Phase F was added to the mixture of step 6 and the mixture was mixed using a propel until the mixture was homogenous.
8. The mixture was cooled to room temperature.

TABLE 2

Conventional Sunscreen

| Phase | Ingredient | Composition 6 (% w/w) |
|---|---|---|
| A | Water | 55.65 |
| | Keltrol[1] | 0.2 |
| B | Micromerol[2] | 5 |
| | Halosol 1%[2] | 1.25 |
| | Hempene Na-2[3] | 0.05 |
| | ExCyte Heather Extract MG[3] | 1.5 |
| | Glycerin[4] | 1 |
| | Germazide MPB[2] | 1.25 |
| | Seamolient CL[2] | 0.75 |
| | Phytic acid[5] | 0.025 |
| C | DC 345 fluid[4] | 5 |
| | IPP[6] | 7 |

TABLE 2-continued

Conventional Sunscreen

| Phase | Ingredient | Composition 6 (% w/w) |
|---|---|---|
| | Stearic acid[7] | 3 |
| | Alpha bisabolol[8] | 0.1 |
| | Soybean oil[9] | 2 |
| | Emersol 315[10] | 0.1 |
| | Emersol 221[10] | 0.05 |
| | Amphisol K[11] | 0.8 |
| | Polyolprepolymer 2[12] | 0.3 |
| | Escalol 557[13] | 7.5 |
| | Parsol 1789[14] | 3 |
| | Silox lemon balm[2] | 1.25 |
| | Basis LP 20 H[15] | 0.375 |
| D | Pemulen TR-1[6] | 0.2 |
| E | Water | 1 |
| | TEA 99%[16] | 0.45 |
| F | A + E liposomes[2] | 0.5 |
| | C + E liposomes[2] | 0.5 |
| | Blue algae extract[2] | 0.2 |
| | Total Percentage | 100.00 |

[1]Kelco, San Diego, California;
[2]Collaborative Laboratories, Inc., Stony Brook, NY;
[3]J. Lowenstein, Brooklyn, New York;
[4]Ashland, Aston, Pennsylvania;
[5]Sigma, St. Louis, Missouri;
[6]Protameen Chemicals, Totowa, New Jersey;
[7]Pride, Holtsville, New York;
[8]Dragoco, Totowa, New Jersey;
[9]Welch Holme Clark, Newark, New Jersey;
[10]UPI, Edison, New Jersey;
[11]Chem International, New York;
[12]Barnet, Englewood Cliffs, New Jersey:
[13]ISP, Wayne, New Jersey;
[14]Hoffman La Roche, Nutley, New Jersey;
[15]Ikeda, Island Park, New York;
[16]KCI, Glenrock, New Jersey.

C. Preparation of Surfactant-Free Sunscreen Formulations

Compositions 7–23 in Tables 3–6 are surfactant-free finished goods formulations of the present invention containing dispersions prepared using high pressure/high shear technology. Compositions 7–9 in Table 3 were prepared as follows:
1. With propeller agitation, water in Phase A was added to the moisturizing base.
2. The remaining ingredients in Phase A were added sequentially and mixed until completely uniform.
3. With paddle blade agitation, the ingredients in Phase B were added to Phase A (step 2) and mixed until completely uniform.

TABLE 3

| | SPF Lotion and Spray (% w/w) | COMPOSITION | | |
|---|---|---|---|---|
| Phase | Ingredient | 7 | 8 | 9 |
| A | Moisturizing Base[2] | 35.25 | 35.35 | 10.50 |
| | Water | 17.25 | 18.15 | 46.75 |
| | AMC ™ [2] | 1.00 | 1.00 | 4.00 |
| B | AM 200[2] | 14.50 | 9.50 | 5.00 |
| | AM 300[2] | 6.50 | 4.50 | 5.50 |
| | AM 400[2] | 4.50 | 11.50 | 4.00 |
| | AM 500[2] | — | — | 3.00 |
| | AM 700[2] | 1.00 | — | 1.00 |

TABLE 3-continued

| Phase | SPF Lotion and Spray (% w/w) Ingredient | COMPOSITION 7 | 8 | 9 |
|---|---|---|---|---|
|  | Germaben ® 2[1] | — | — | 0.25 |
|  | Composition 2 | 20.00 | 20.00 | 20.00 |
|  | Total Percentage | 100.00 | 100.00 | 100.00 |

[1]ISP Corporation, New Jersey, USA.
[2]Collaborative Laboratories, Inc., Stony Brook, NY.

Compositions 10–12 in Table 4 were prepared as follows:

1. With propeller agitation, water in Phase A was added to the moisturizing base.
2. The remaining ingredients in Phase A were added sequentially and mixed until completely uniform.
3. With paddle blade agitation, the ingredients in Phase B were added to Phase A (step 2) and mixed until homogenous.
4. The ingredients in Phase C were sequentially added to Phase (A+B) (step 3) and mixed until completely uniform.

TABLE 4

| Phase | SPF Moisturizing Creams (% w/w) Ingredient | COMPOSITION 10 | 11 | 12 |
|---|---|---|---|---|
| A | Moisturizing Base[2] | 38.00 | 40.00 | 41.00 |
|  | Water | 8.25 | 6.00 | 5.00 |
|  | AMC ™ [2] | 1.75 | 2.00 | 2.00 |
|  | AM 900[2] | 6.00 | 6.00 | 6.00 |
| B | AM 200[2] | 6.00 | 6.00 | 6.00 |
|  | AM 300[2] | 6.00 | 3.00 | 3.00 |
|  | AM 500[2] | 2.50 | — | — |
|  | AM 700[2] | 6.50 | 7.00 | 7.00 |
| C | Aculyn ™ 44[1] | — | 1.00 | 1.00 |
|  | 25% Celluflow in BG[3] | — | 3.50 | 3.50 |
|  | Composition 2 | 20.00 | 20.00 | 20.00 |
|  | Sansurf ™ DMG[2] | 1.00 | 1.00 | 1.00 |
|  | Sansurf ™ Vitamin E[2] | 1.00 | 1.00 | 1.00 |
|  | Seamollient ® [2] | 1.00 | 1.50 | 1.50 |
|  | Total Percentage | 100.00 | 100.00 | 100.00 |

[1]ISP Corporation, New Jersey, USA.
[2]Collaborative Laboratories, Inc., Stony Brook, NY.
[3]Chisso Corporation, Tokyo, Japan.

Compositions 13–17 in Table 5 were prepared as follows:

1. With propeller agitation, water in Phase A was added to the moisturizing base.
2. The remaining ingredients in Phase A were added sequentially and mixed until completely uniform.
3. With paddle blade agitation, the ingredients in Phase B were sequentially added to Phase A (step 2) and mixed until homogenous.
4. The ingredients in Phase C were sequentially added to Phase (A+B) (step 3) and mixed until completely uniform.

TABLE 5

| | | COMPOSITION | | | | |
|---|---|---|---|---|---|---|
| Phase | Moisturizers with SPF 15 or greater (% w/w) Ingredient | 13 Moist Cream (Very Dry) | 14 Moist Lotion (Very Oily) | 15 Moist Cream (Dry) | 16 Moist Cream (Very Dry) | 17 Moist Lotion (Very Dry) |
| A | Moisturizing Base[1] | 44.00 | — | 48.40 | — | 32.55 |
|  | Lotion Base[1] | — | 35.00 | — | 37.00 | 4.75 |
|  | Deionized Water | 1.65 | 29.30 | 0.25 | 0.81 | 5.00 |
|  | AMC[1] | 4.75 | 5.00 | 4.75 | 4.25 | |
|  | AM 900[1] | 13.00 | — | 10.00 | 7.90 | |
| B | AM 100[1] | — | 5.00 | — | 7.13 | |
|  | AM 200[1] | — | 5.00 | — | 7.13 | |
|  | AM 300[1] | — | — | — | 7.13 | |
|  | AM 400[1] | 6.50 | — | 6.50 | — | |
|  | AM 500[1] | | | | | 10.00 |
|  | AM 600[1] | 2.75 | — | 2.75 | — | 10.00 |
|  | AM 700[1] | | | | | 10.00 |
|  | Composition 2 | 20.00 | 20.00 | 20.00 | 20.00 | 20.00 |
| C | Cocoa Butter[2] | | | | | 5.00 |
|  | Germazide MPG[1] | 0.70 | 0.70 | 0.70 | 0.70 | 0.80 |
|  | Butylene Glycol[3] | 4.75 | — | 4.75 | 4.25 | |
|  | Seamollient[1] | 1.90 | | 1.90 | 1.70 | |
|  | SS Bisabolol[1] | | | | 2.00 | 2.00 |
|  | TOTALS | 100.00 | 100.00 | 100.00 | 100.00 | 100.00 |

[1]Collaborative Laboratories, Stony Brook; NY;
[2]Universal Preservatives, Edison, NJ;
[3]Kramer Chemicals, Glen Rock, NJ Compositions 18–23 in Table 6 were prepared as follows:
1. With propeller agitation, water in Phase A was added to the moisturizing base.
2. The remaining ingredients in Phase A were added sequentially and mixed until completely uniform.
3. With paddle blade agitation, the ingredients in Phase B were sequentially added to Phase A (step 2) and mixed until homogenous.

TABLE 6

Sunscreen Compositions (% w/w)

| Phase | Ingredient | 18 | 19 | 20 | 21 | 22 | 23 |
|---|---|---|---|---|---|---|---|
| A | Moisturizing Base[1] | 35.25 | 35.25 | 35.25 | 35.25 | 35.25 | 35.25 |
|   | D.I. Distilled Water | 9.25 | 0.00 | 0.00 | 4.25 | 23.25 | 18.25 |
|   | AMC[1] | 1.00 | 1.00 | 1.00 | 1.00 | 1.00 | 1.00 |
| B | AM-200[1] | 9.50 | 9.50 | 9.50 | 9.50 | 9.50 | 9.50 |
|   | AM-300[1] | 4.50 | 4.50 | 4.50 | 4.50 | 4.50 | 4.50 |
|   | AM-400[1] | 11.50 | 10.75 | 9.75 | 11.50 | 11.50 | 11.50 |
|   | Octacrylene[2] | 4.00 | 4.00 | 0.00 | 4.00 | 0.00 | 0.00 |
|   | Composition 5 | 25.00 | 25.00 | 0.00 | 0.00 | 0.00 | 0.00 |
|   | TioSperse Ultra[1] | 0.00 | 10.00 | 10.00 | 0.00 | 0.00 | 0.00 |
|   | Composition 4 | 0.00 | 0.00 | 30.00 | 0.00 | 0.00 | 0.00 |
|   | Composition 3 | 0.00 | 0.00 | 0.00 | 30.00 | 0.00 | 0.00 |
|   | SS-OMC-50[1] | 0.00 | 0.00 | 0.00 | 0.00 | 15.00 | 0.00 |
|   | Composition 2 | 0.00 | 0.00 | 0.00 | 0.00 | 0.00 | 20.00 |
|   | TOTAL | 100.00 | 100.00 | 100.00 | 100.00 | 100.00 | 100.00 |

[1]Collaborative Laboratories, Inc., Stony Brook; NY
[2]BASF, Mt. Olive, NJ

Example 2

SPF Values of the Compositions of the Present Invention

Panels were convened to evaluate the effectiveness of seven test materials as sunscreen products by determining the static and/or water resistant Sun Protection Factor (SPF) on human skin according to a procedure similar to that in the Tentative Final Monograph, "Sunscreen Drug Products For Over-The-Counter Human Drugs", (Federal Register Volume 58, Number 90 pages 28194–28302, 1993) using a Xenon arc solar simulator as the UV source. This testing was conducted prior to and immediately following an immersion experiment which was carried out under controlled conditions (Water Resistant Testing) as described in the TFM monograph. Five subjects were tested in these studies.

A. Materials and Methods
   1) Test Compositions
   Sunscreen Compositions 6, 13, 14, 15, 16, 17, 18, 19, 20, 21, 22 and 23 from Example 1 were tested.
   2) Test Subjects
   Panel Demographics:
Number of subjects enrolled . . . 5
Number of subjects completing study . . . 5
   i) Standards for Inclusion in the Study:
    a. Individuals between the ages of 18 and 55.
    b. Individuals free of any dermatological or systemic disorder which would interfere with the results, at the discretion of the investigator.
    c. Individuals free of any acute or chronic disease that might interfere with or increase the risk of study participation.
    d. Individuals with Fitzpatrick's skin type I, II, and III only.
    e. Individuals with no uneven skin tones, pigmentation, scars, other irregularities or hair in test site areas that would interfere with SPF determination.
    f. Individuals who will complete a preliminary medical history form and are in general good health.
    g. Individuals who will read, understand and sign an informed consent document relating to the specific type of study they are subscribing.
    h. Individuals able to cooperate with the investigator and research staff, be willing to have test materials applied according to the protocol, and complete the full course of the study.
    i. Individuals willing to refrain from using any sunscreen products, sunbathing or tanning bed use, 24 hours prior to study initiation and the entire duration of the study.
    j. Individuals with excessive hair on their back who are willing to clip or shave their hair.
   ii). Standards of Exclusion from the Study:
    a. Individuals who are under doctor's care.
    b. Individuals who are currently taking any medication (topical or systemic) that may mask or interfere with the test results.
    c. Subjects with a history of any form of skin cancer, melanoma, lupus, psoriasis, connective tissue disease, diabetes or any disease that would increase the risk associated with study participation.
    d. Individuals diagnosed with chronic skin allergies.
    e. Individuals with a history of adverse effects upon sun exposure.
    f. Female volunteers who indicate that they are pregnant or nursing.
    g. Individuals with blemishes, nevi, sunburn, suntan, scars, moles, active dermal lesions or uneven pigmentation in the test sites.
    h. Individuals with known hypersensitivity to any sunscreen products. A trained technician performed a physical examination of the panelist's back to determine if study eligibility criteria were satisfied.

Panel Composition:

Healthy volunteers over the age of 18 years were recruited for this study. The panel consisted of fair-skin individuals with skin types I, II or III defined as follows (Federal Register Vol. 58, No. 90: 28299, 1993).*

Type I—Always burns easily; never tans
Type II—Always burns easily; tans minimally
Type III—Burns moderately; tans gradually
*—Based on the first 30 to 45 minutes sun exposure after a winter season of no sun exposure.

3) Artificial Light Source

The light source employed was a 150 watt Xenon Arc Solar Simulator (Solar Light Co., Philadelphia, Pa., Model 12S, Model 14S or Model 600) having a continuous emission spectrum in the UVB range from 290 to 320 nm. Xenon arc was selected on the basis of its black body radiation temperature of 6000° K. which produced continuous UV spectra (All wavelengths) substantially equivalent to that of natural sunlight.

This device was equipped with a dichroic mirror (which reflects all radiation below 400 nm) and worked in conjunction with a 1 mm thick Schott WG-320 filter (which absorbed all radiation below 290 nm) to produce simulation of the solar UVA-UVB spectrum. A 1 mm thick UG 11 filter (black lens) was added to remove reflected (infra-red, greater than 700 nm) heat and remaining visible radiation. UVB radiation was monitored continuously during exposure using a Model DCS-1 Sunburn UV Meter/Dose Controller System (Solar Light Co.) formerly known as the Robertson-Berger Sunburn Meter (R-B meter). Measurements were taken at a position within 8 mm from the surface of the skin. The field of irradiation was 1 cm in diameter. The solar simulator was allowed a warm up time of at least 15 minutes before use and power supply output was recorded.

Realignment of the Light Sources and calibration of the sunburn meters were conducted semi-annually by independent certification facilities and more often as necessary at the discretion of the operating technician or investigator.

4) Static SPF Determination (Including 8% Homosalate Standard)

The infrascapular area of the back to the right and left of the midline was used. Within this area, 50 cm$^2$ rectangular test sites were delineated with a gentian violet surgical skin marker. Sites were observed to ensure uniform pigmentation, skin tone and texture, and absence of warts, moles, nevi, scars, blemishes and active dermal lesions. Any areas that might be expected to produce erratic results were not used for UV exposures.

The procedure for this study is outlined in the Federal Register, Vol. 58: No. 90, 28194–28302. One test site area served to determine each subject's Minimal Erythema Dose (MED). A minimum of five UV exposures was administered within this site. The individual subject's MED was the shortest time of exposure that produces minimally perceptible erythema at 22 to 24 hours post irradiation.

The test material and 8% homosalate standard were shaken and/or swirled with a glass rod before use and were evenly applied using plastic volumetric syringes to rectangular areas measuring 5 cm×10 cm (50 cm$^2$) for a final concentration of 2.0 mg/cm$^2$. Evenness of application was verified by observation with a Woods Lamp.

Fifteen minutes after application, an unprotected site received a series of seven UV exposures based upon previously determined MED. The UV exposures for test products, 8% homosalate standard was calculated from previously determined MED and the intended SPF as follows:

SPF 4: MED times 0.64x, 0.80x, 0.90x, 1.00x, 1.10x, 1.25x and 1.56x

SPF 15: MED times 0.69x, 0.83x, 0.91x, 1.00x, 1.09x, 1.20x and 1.44x where x equals the expected SPF of the product.

On the actual day of testing another series of exposures similar to the one given on the previous day was administered to an adjacent untreated site of unprotected skin to re-determine the MED. An adjacent test site was then selected to perform a static determination on the test substance, as above, prior to the immersion test.

5) Water Resistance

This test was employed to determine the substantivity of a test product and its ability to resist water immersion. On the day of the test, following exposure of the homosalate standard, MED's and static determination, another area measuring 5 cm×10 cm, was designated. Again the test product was spread uniformly throughout the area at a concentration of 2.0 mg/cm$^2$, then allowed a fifteen minute drying period as before. One other adjacent site was selected to perform a waterproof SPF bracketing the intended label claim of the test material.

Immersion was achieved indoors in a whirlpool tub with water circulating by a 1 h.p. pump at 3450 RPM. Each panelist spent twenty minutes in the water, immediately followed by a twenty minute rest period out of the water until a total of forty minutes in the water was achieved. The whirlpool bath was maintained at an average temperature of 74–89° F. at moderate agitation. After the last immersion, the test sites were air dried without toweling for at least fifteen minutes prior to irradiation. The water and air temperatures and relative humidity were recorded.

The second series of test material exposures was administered to the protected area. The exact series of exposures given was determined by the MED and the expected SPF of the product as before.

5) Evaluation of Responses

Twenty-two to twenty-four hours post exposure, the subjects were instructed to return to the testing facility for evaluation of delayed erythemic responses. The technician who evaluated the MED did not know the identity of the test product application sites and UV exposures. Also he/she was not the same person to have applied the sunscreen product to the test site or to have administered the doses of UV radiation.

$$SPF = \frac{\text{Protected } MED}{\text{Final unprotected } MED}$$

Visual grading scale:
0=No Erythema
?=Questionable Erythema
1=Minimal Erythema
2=Slight Erythema
3=Well-Defined Erythema
4=Erythema and Edema
5=Erythema and Edema in vesicles 6) Calculation of SPF and PCD The mean SPF value (x) was calculated using a minimum of 20 evaluable subjects per formulation. The standard deviation was determined (s). The upper 5% point was obtained from the t distribution table with n−1 degrees of freedom (t). First, A was calculated as follows:

$$A = \frac{(t)(s)}{\sqrt{n}}$$

Therefore, the label SPF was the largest whole number less than the mean SPF minus A.

Label *SPF*=Mean *SPF*–*A*

The Product Category Designation (PCD), for labeling purposes, was assigned based on the mean SPF and PCD ranking according to the TFM. Classification may be Ultra High, Very High, High, Moderate or Minimal. Only three test panelists were included in this study, therefore no-PCD was assigned.

Rejection criteria: Panelist's results were rejected and the panelist was replaced if:
1. An exposure series failed to elicit an MED response on the untreated skin. The test was considered a technical failure even if the MED response was observed in the protected site.
2. The responses on the protected area were randomly absent, indicating uneven product spreading, non-constant light irradiance or unstable product.
3. All exposures in a series elicited responses—thus prohibiting any MED calculation.

B. Results and Conclusion

The results in Table 7 show that surfactant-free compositions 13–23 demonstrated a significantly greater SPF value than the conventional emulsion formulation containing the same level of sunscreen, Composition 6. Surfactant-free compositions 13–18, which contain the sunscreen dispersion of Example 2, were demonstrated to very water resistant since little to no SPF protection was lost even after repeated exposures to water.

TABLE 7

| | Composition | | | | | | | | | | |
|---|---|---|---|---|---|---|---|---|---|---|---|
| | 6 | 13 | 14 | 15 | 16 | 17 | 18 | 19 | 20 | 21 | 22 | 23 |
| Static SPF | 8.18 | 20.28 | 20.00 | 20.56 | 20.28 | 20.28 | 16.85 | 21.40 | 35.90 | 34.39 | 46.89 | 15.54 |
| Water-Resistant SPF | — | 19.72 | 19.48 | 20.00 | 18.92 | 18.68 | 16.65 | — | — | — | — | — |

The results demonstrate that the surfactant-free compositions containing the dispersions of sunscreen active agents maintained higher SPF values and water resistance even when aesthetic modifying agents, such as oils and waxes, in the dispersions were varied. This is not the case for standard emulsion systems.

What is claimed is:

1. A sunscreen formulation comprising:
   (a) a dispersion, the dispersion comprising a sunscreen active agent; and
   (b) a base composition, the base composition comprising
      (i) a rheological modifying agent, and
      (ii) water,
wherein the dispersion has a particle size of less than 1000 nanometers (nm) and wherein the sunscreen formulation free of surfactants.

2. The formulation of claim 1 wherein the dispersion comprises the sunscreen active agent in the form of suspended particles, the suspended particles being present in an amount of from about 1.0 to about 60% by weight of suspended particles, based upon 100% weight of total dispersion.

3. The formulation of claim 1 wherein the base composition comprises from about 0.01 to about 10% by weight of the rheological modifying agent.

4. The formulation of claim 1 wherein the base composition comprises from about 20 to about 99.99% by weight of water.

5. The formulation of claim 1 wherein the dispersion comprises from about 10 to about 50% by weight of the total formulation.

6. The formulation of claim 1 wherein the base composition comprises from about 5 to about 80% by weight of the total formulation.

7. The sunscreen formulation of claim 1, wherein the sunscreen formulation is water resistant.

8. The sunscreen formulation of claim 1, wherein the dispersion is produced using high pressure, high shear or a combination thereof.

9. The sunscreen formulation of claim 1, wherein the sunscreen active agent is selected from one or more members of the group consisting of aminobenzoic acid, cinoxate, dioxybenzone, homosalate, methyl anthranilate, octocrylene, octisalate, oxybenzone, padimate O, phenylbenzimidazole sulfonic acid, sulisobenzone, trolamine salicylate, octylmethoxycinnamate, methoxydibenzoylmethane, ethylmethoxycinnamate and butylmethoxydibenzoylmethane.

10. The sunscreen formulation of claim 1, wherein the dispersion further comprises water, ethylmethoxycinnamate, and butylmethoxydibenzoylmethane.

11. The sunscreen formulation of claim 1, wherein the rheological modifying agent comprises a hydrophilic gelling agent.

12. The sunscreen formulation of claim 11, wherein the hydrophilic gelling agent comprises one or more members selected from the group consisting of carboxyvinyl polymers, acrylic copolymers, polyacrylamides, polysaccharides, natural gums and clays.

13. The sunscreen formulation of claim 1, wherein the rheological modifying agent comprises a phosphorylated starch derivative.

14. The sunscreen formulation of claim 13, wherein the phosphorylated starch derivative is hydroxypropyl distarch phosphate.

15. The sunscreen formulation of claim 1, wherein the rheological modifying agent is selected from the one or more members of the group consisting of sodium hyaluronate, acrylates/$C_{10}$–$C_{30}$ alkyl acrylate crosspolymer, xanthum gum, cholesterol, hydroxypropyl distarch phosphate, carbomer, guar hydroxy propyltrimonium chloride, hydroxypropyl guar and sodium hydroxypropyl starch phosphate.

16. The sunscreen formulation of claim 1 further comprising one or more conditioning agents selected from the group consisting of sodium hyaluronate, algae extract, cyclomethicone, isopropyl palmitate, bisabolol, soybean oil, linoleic acid, PPG-12/saturated methylene diphenyldiisocyanate copolymer, liposomes and, phospholipids, urea, cyclomethicone, dimethicone, cyclopentasiloxane, amodimethicone, trideceth-12, cetrimonium chloride, diisostearoyl trimethylolpropane siloxy silicate, diphenyl dimethicone, propylene glycol and glycerin.

17. The sunscreen formulation of claim 1 further comprising a preservative which is selected from one or more members of the group consisting of chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methychloroisothiazolinone and methylisothiazolinone.

18. The sunscreen formulation of claim 1 further comprising a pH adjuster, an emollient, a chelating agent, a colorant, a fragrance, an odor masking agent, or any combination thereof.

19. A method of protecting skin or hair from ultraviolet radiation comprising applying an effective amount of the sunscreen formulation of claim 1 to the skin or hair.

20. The method of claim 19, wherein the dispersion is produced using high pressure, high shear or a combination thereof.

21. The method of claim 20, wherein the dispersion of the sunscreen formulation comprises water, ethylmethoxycinnamate, and butylmethoxydibenzoylmethane.

22. The method of claim 19, wherein the sunscreen active of the sunscreen formulation is selected from one or more of the group consisting of aminobenzoic acid, cinoxate, dioxybenzone, homosalate, menthyl anthranilate, octocrylene, octisalate, oxybenzone, padimate O, phenylbenzimidazole sulfonic acid, sulisobenzone, trolamine salicylate, octylmethoxycinnamate, methoxydibenzoylmethane, ethylmethoxycinnamate, and butylmethoxydibenzoylmethane.

23. The method of claim 19, wherein the rheological modifying agent of the sunscreen formulation comprises a hydrophilic gelling agent.

24. The method of claim 23, wherein the hydrophilic gelling agent of the sunscreen formulation comprises one or more members selected from the group consisting of carboxyvinyl polymers, acrylic copolymers, polyacrylamides, polysaccharides, natural gums and clays.

25. The method claim 19, wherein the rheological modifying agent of the sunscreen formulation comprises a phosphorylated starch derivative.

26. The method of claim 25, wherein the phosphorylated starch derivative of the sunscreen formulation is hydroxypropyl distarch phosphate.

27. The method of claim 19, wherein the rheological modifying agent of the sunscreen formulation comprises one or more members selected from the group consisting of sodium hyaluronate, acrylates/$C_{10}$–$C_{30}$ alkyl acrylate crosspolymer, xanthum gum, cholesterol, hydroxypropyl distarch phosphate, carbomer, guar hydroxy propyltrimonium chloride, hydroxypropyl guar and sodium hydroxypropyl starch phosphate.

28. The method of claim 19, wherein the sunscreen formulation further comprises one or more conditioning agents selected from the group consisting of sodium hyaluronate, algae extract, cyclomethicone, isopropyl palmitate, bisabolol, soybean oil, linoleic acid, PPG-12/saturated methylene diphenyldiissocyanate copolymer, liposomes and, phospholipids, urea, cyclomethicone, dimethicone, cyclopentasiloxane, amodimethicone, trideceth-12, cetrimonium chloride, diisostearoyl trimethylolpropane siloxy silicate, diphenyl dimethicone, propylene glycol and glycerin.

29. The method of claim 19, wherein the sunscreen formulation further comprises a preservative which is one or more members selected from the group consisting of chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylchloroisothiazolinone and methylisothiazolinone.

30. The method of claim 19, wherein the sunscreen formulation further comprises a pH adjuster, an emollient, a chelating agent, a colorant, a fragrance, an odor masking agent, and any combination of any of the foregoing.

31. The method of claim 19, wherein the sunscreen formulation is water resistant.

32. The sunscreen composition of claim 1, wherein the dispersion has a particle size between about 50 nm and about 1000 nm.

33. The sunscreen composition of claim 1, wherein the dispersion has a particle size between about 300 nm and about 800 nm.

34. The formulation of claim 1 wherein the base composition comprises from about 0.001 to about 50% by weight of the rheological modifying agent.

35. The formulation of claim 1 wherein the dispersion comprises from about 1% to about 60% by weight of the total formulation.

* * * * *